United States Patent [19]

Klopping

[11] 4,060,625

[45] Nov. 29, 1977

[54] MIXTURES OF METHYL 2-BENZIMIDAZOLECARBAMATE AND ETHYLENEBISDITHIO-CARBAMIC ACID SALTS AS FOLIAR FUNGICIDES

[75] Inventor: Hein Louis Klopping, Wilmington, Del.

[73] Assignee: E. I. Du Pont de Nemours and Company, Wilmington, Del.

[21] Appl. No.: 676,143

[22] Filed: Apr. 12, 1976

Related U.S. Application Data

[63] Continuation of Ser. No. 491,527, July 24, 1974, abandoned, which is a continuation-in-part of Ser. No. 324,826, Jan. 18, 1973, abandoned, which is a continuation-in-part of Ser. No. 260,196, June 6, 1972, abandoned, which is a continuation-in-part of Ser. No. 861,791, Sept. 29, 1969, abandoned, which is a continuation-in-part of Ser. No. 727,036, May 6, 1968, abandoned, which is a continuation-in-part of Ser. No. 629,914, April 11, 1967, abandoned.

[51] Int. Cl.$^2$ .......................... A01N 9/22; A01N 9/12
[52] U.S. Cl. ................................ 424/273 R; 424/286
[58] Field of Search ....................... 424/273, 287, 289

[56] References Cited

U.S. PATENT DOCUMENTS

| | | | |
|---|---|---|---|
| 2,933,502 | 4/1960 | Klopping | 260/299 |
| 2,933,504 | 4/1960 | Klopping | 260/309.2 |

Primary Examiner—V. D. Turner

[57] ABSTRACT

Mixtures of methyl 2-benzimidazolecarbamate with the manganous or zinc salts of ethylenebisdithiocarbamic acid, i.e., maneb or zineb, are effective as foliar fungicides.

6 Claims, No Drawings

MIXTURES OF METHYL 2-BENZIMIDAZOLECARBAMATE AND ETHYLENEBISDITHIO-CARBAMIC ACID SALTS AS FOLIAR FUNGICIDES

CROSS REFERENCE TO RELATED APPLICATIONS

This application is a continuation of application Ser. No. 491,527, filed July 24, 1974, now abandoned which is a continuation-in-part of my copending application Ser. No. 324,826, filed Jan. 18, 1973, now abandoned which is a continuation-in-part of my application Ser. No. 260,196, filed June 6, 1972, now abandoned, which is a continuation-in-part of abandoned application Ser. No. 861,791, filed Sept. 29, 1969, which is a continuation-in-part of abandoned application Ser. No. 727,036, filed May 6, 1968, which is a continuation-in-part of abandoned application Ser. No. 629,914, filed Apr. 11, 1967.

BACKGROUND OF THE INVENTION

Most crop and ornamental plants are subject to attack by several pathogenic fungi. The diversity of these organisms and their potential for inciting serious disorders in combination or singly has resulted in the need for broad-spectrum disease control. Although there are available numerous chemical compounds (fungicides) which aid in preventing diseases of plants, each of these has practical deficiencies which restrict its use. The inability of any one fungicide to control all of the potentially serious pathogens on one host makes the use of combinations or mixtures of fungicides a part of normal control practice.

SUMMARY OF THE INVENTION

The combinations or mixtures of the invention involve methyl 2-benzimidazolecarbamate, i.e.:

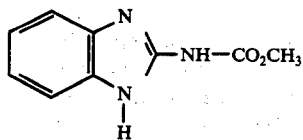

with the manganous or zinc salts of ethylenebisdithiocarbamic acid, i.e., maneb or zineb. The mixtures can be used at concentrations lower than are required for control with either component used singly.

The preferred mixture in view of its high fungicidal activity is the mixture of methyl 2-benzimidazolecarbamate with maneb.

DETAILED DESCRIPTION OF THE INVENTION

Methyl 2-benzimidazolecarbamate can be prepared by any of a variety of methods known in the art. Loux, U.S. Pat. No. 3,010,968, discloses the reaction of o-phenylenediamine and methyl 2-methylthiopseudoureacarboxylate produces methyl 2-benzimidazolecarbamate.

Maneb and zineb are well-known fungicides and the art methods can be used for their preparation. Thus maneb and zineb are conventionally prepared by reacting ethylene diamine and carbon disulfide in the presence of a free base and then reacting the salt formed with a manganous or zinc salt. The process for making maneb is set forth in greater detail in U.S. Pat. No. 2,504,404.

In the mixtures of the invention, the range of proportions can be from 1:1 to 1:20 of the methyl 2-benzimidazolecarbamate to the maneb or zineb. The preferred ratios are from 1:1 to 1:10 and the most preferred are from 1:2 to 1:6.

The preferred rates of application for the combinations or mixtures of this invention foliage, stems, and/or fruit of living plants range from 10 to 10,000 ppm of total active ingredient in the spray or dip fluid, or 0.1 to 10 kilos of active ingredient per hectare. More preferred rates are in the range of 20 to 5,000 ppm or 0.25 to 5 kilos per hectare. The most preferred rates are in the range of 50 to 2,000 ppm or 0.5 to 2 kilos per hectare.

The proper choice of ratios and rates will vary depending on the host and environmental conditions. Those skilled in the art of protecting plants from disease will readily make a choice consistent with experience. The unexpected factor which must be considered in that choice of rates is the unusual effectiveness of the mixtures of this invention over the normal additive effects.

The many fungi against which the mixtures of this invention are active may be represented by, but is not intended to be limited to, the following: Plasmopara viticola, which causes downy mildew of grape; Phytophthora infestans which causes late blight of potato and tomato; Phytophthora parasitica and P. citrophthora, which cause foot rot and brown rot of citrus; Phytophthora phaseoli, which causes downy mildew of lima bean; Pseudoperonospora cubensis, which causes downy mildew of cucurbits; Personospora effusa, which causes downy mildew of spinach; Alternaria solani, which causes early blight of tomato and potato; Helminthosporium spp., which cause leaf spots of many grasses and cereals; Venturia inaequalis, which causes apple scab; Podosphaera leucotricha, which causes powdery mildew on apple; Uromyces phaseoli, which causes bean rust; Cercospora apii, which causes early blight of celery; Cercospora beticola, which causes leaf spot of sugar beets; Sclerotinia sclerotiorum, which causes rot of vegetable crops, such as lettuce, beans, carrots, and celery; Colletotrichum spp., which cause anthracnose of fruits and vegetables, such as beans, tomatoes and coffee; Septoria apii, which causes late blight of celery; cercospora musae, which causes Sigotoka disease of banana; Piricularia sp., which causes Johnson spot on banana; Erysiphe cichoracearum, which causes powdery mildew on cantaloupe and other cucurbit crops; Penicillium digitatum, Phomopsis spp., and Diplodia natalensis, which cause fruit rots on citrus; Ceratostomella ulmi, which causes Dutch elm diesase; Sphaerotheca humuli, which causes powdery mildew on roses; Diplocarpon rosae, which causes black spot on roses; Ramularia sp., which causes leaf spots on ornamental plants; Botrytis cinerea, which causes blossom and fruit rots of ornamentals, fruits and vegetables; Uncinula necator, which causes powdery mildew on grapes; Guignardia bidwellii, which causes grape black rot; Melonconium fuligineum, which causes white rot of grapes; Coccomyces hiemalis, which causes cherry leaf spot; Cytospora sp., which cause cankers of trees; Cladosporium carpophilum, which causes peach scab; Fusicladium effusum, which causes pecan scab; Erysiphe graminis, which causes powdery mildew on cereals; Monolinia (Sclerotinia) laxa and M. fructicola, which cause brown rot of stone fruits, such as peaches, cherries and apricots; Pseudopeziza ribes, which causes leaf spot on gooseberry; Piricularia

*oryzae,* which causes rice blast; *Puccinia recondita, P. coronata* and *P. glumarum,* which cause leaf rusts of wheat, oats and grasses, respectively; *Puccinia graminis tritici,* which causes stem rust of wheat; *Claviceps purpurea,* which causes ergot of rye and grasses; *Asperigillus niger,* which causes cotton boll rot as well as decay following wounding in many plant tissues; *Aspergillus flavus,* which causes mold growth on peanuts, as well as on other food and feed materials; *Aspergillus terreus,* which is common in soil and attacks vegetable matter; *Tilletia caries* and other *Tilletia* species, which cause common bunt of wheat; *Ustilago tricici, Ustilago nigra, Ustilago avena* (and other *Ustilago* species), which cause loose smut of wheat, barley, and oats, respectively; *Urocystis tritici* and other *Urocystis* species, which cause loose smut of wheat; *Sphacelotheca sorghi,* which causes covered smut of sorghum; *Ustilago hordei* and *Ustilago kolleri,* which cause covered smut of barley and oats, respectively; *Pithomyces chartorum,* which is present in turf, pastures, and other grassy areas and is known to have several secondary effects; *Gloeodes pomigena,* which causes sooty blotch on apples; *Physalospora obtusa,* which causes black rot on apples; and *Microthyriella rubi,* which causes flyspeck on apples.

The mixtures of the invention are conveniently formulated by preparing a tank mix of conventional formulations of each of the active ingredients, i.e., a tank mix of the active ingredients with diluents.

Formulations of maneb and zineb are well known, thus wettable powders and dusts are disclosed in U.S. Pat. Nos. 2,504,404; 2,665,285; 2,719,822; 2,974,156; 3,085,042 and 3,173,832.

Formulations of methyl 2-benzimidazolecarbamate are also known and can be prepared as disclosed in U.S. Pat. No. 3,657,443.

If desired, dusts can be prepared by mixing the active ingredients, grinding and then adding inert solids or diluents and blending. These compositions can also contain various conditioning agents and surface active agents. Suitable diluents include talc and sucrose.

Specific examples of the useful combinations and mixtures of this invention are set forth below. All parts are parts by weight unless otherwise indicated.

EXAMPLE 1

Commercial formulations of methyl 2-benzimidazolecarbamate and manganous ethylenebisthiocarbamate (maneb) are combined as a mixture in the spray tank. The concentration of this mixed suspension is 200 ppm of the active ingredient methyl 2-benzimidazolecarbamate and 1000 ppm of the active ingredient, maneb.

A uniform planting of grape vines is selected and one row of vines is designated to receive treatments with the mixture of fungicides described above. Treatments are applied to the designated vines to the point of run-off every 14 days from blossom time until harvest. An examination of the vines and fruit at harvest reveals that those treated with the mixture are growing vigorously, with large healthy leaves and a normal crop of well-developed grapes. On the other hand, the adjacent vines which had not been treated with the mixture are severely damaged by several diseases. The leaves are necrotic and dried up because of attack from downy mildew (*Plasmopara viticola*). The growing tips and some fruit clusters are distorted and discolored due to heavy infections with the powdery mildew fungus, (*Uncinula necator*). The fruit are destroyed by the attack of several fungi, including the mildews and *Botrytis cinerea.*

The zinc ethylenebisdithiocarbamate (zineb) can be combined in the mixture in place of the maneb with similar results.

EXAMPLE 2

The mixture described in Example 1 is applied to selected plot areas to the point of run-off in a rice paddy. Two treatments are applied 10 days apart at transplanting, and an additional 3 applications are made during flowering. At harvest the treated plots are compared with rice in the adjacent untreated areas. The plants in the treated plots are strong and healthy with a full crop of disease free heads. On the other hand, the rice which was not treated is badly damaged by leaf spot (*Helminthosporium oryzae*) on old leaves and the yield is reduced to ¼ the normal production due to blast and neck rot (*Piricularia oryzae*). Another disease which contributes to the reduced yield and unhealthy condition of the untreated rice is sheath blight (*Pellicularia sasakii*). The degree of protection from this complex of disease problems by the treatments with the mixture of this invention is outstanding.

EXAMPLE 3

|  | Percent |
|---|---|
| methyl 2-benzimidazolecarbamate | 2 |
| manganous ethylenebisdithio-carbamate | 4 |
| cane sugar | 6 |
| Micaceous talc | 88 |

The two active components and the sugar are first blended, micropulverized and air milled to produce a powder in which substantially all of the active ingredients are present as particles having diameters of 5 microns or less. This powder is then combined with the talc and blended to form a free-flowing, dense dust.

Equivalent dusts may be prepared by substituting the zinc salt of ethylenebisdithiocarbamic acid.

Selected rows in a field of cucumbers are dusted to get good coverage on a weekly schedule with the mixture described above. At harvest time the dusted rows are covered with a heavy canopy of healthy green foliage and the cucumber fruit are of a high quality and disease free. The plants in the rows which were not dusted, on the other hand are destroyed by several diseases. Downy mildew (*Pseudoperonospora cubensis*), powdery mildew (*Erysiphe cichoracearum*) and leaf blight (*Alternaria cucumerina*) completely defoliate the plants and allow the cucumbers to be exposed to sun scalding. Close examination of the untreated fruit reveals extensive damage by scab (*Cladosporium cucumerinum*) and anthracnose (*Colletotrichum lagenarium*). There were also several untreated plants which had died because of gummy stem blight (*Mycosphaerella citrullina*). The high degree of protection against so many different fungus pathogens with such low concentrations of fungicides is unexpected. As indicated previously, the maneb portion of this composition may be substituted with zineb with similar performance.

EXAMPLE 4

The dust from Example 3 is applied lightly but uniformly to individual grape vines on a 14-day schedule during the growing season. The foliage and fruit from these dusted vines remain healthy and produce normal yields. On the other hand, the untreated vines in the same vineyard are badly injured and defoliated due to downy mildew (*Plasmopora viticola*) and powdery mildew (*Uncinula necator*).

EXAMPLE 5

Commercial formulations of methyl 2-benzimidazolecarbamate and manganous ethylenebisdithiocarbamate (maneb) are combined as a mixture in the spray tank. The concentration of this mixed suspension is 300 ppm of the active ingredient methyl 2-benzimidazolecarbamate and 1000 ppm of the active ingredient, maneb.

The mixture of fungicides described above is sprayed on a single row of tomato plants on a weekly schedule. During harvest the treated plants are healthy and producing an abundance of normal fruit. The untreated plants in adjacent rows, on the other hand, are defoliated by Late Blight (*Phytophthora infestans*) and leaf mold (*Cladosporium fulvum*). The fruit are a total loss due to several fungus pathogens including *Phytophthora infestans*, *Botrytis cinerea* and *Colletotrichum phomoides*.

EXAMPLE 6

|  | Percent |
| --- | --- |
| methyl 2-benzimidazolecarbamate | 10 |
| manganous ethylenebisdithiocarbamate | 40 |
| sodium dioctylsulfosuccinate | 2 |
| methylcellulose 15 cps. | 1 |
| sucrose | 47 |

The above components are blended, micropulverized and air milled until the active materials are substantially all below 5 microns. The zinc salt of ethylenebisdithiocarbamic acid may replace the manganous salt in the above composition if desired.

Selected plots in a plantation of bananas are sprayed to the point of run-off with a suspension made from the above mixture. The spray contains 500 ppm of the combined active ingredients. Applications are made every 14 days during the infection period. The treated trees are disease free and support a large healthy crop of bananas. The untreated trees are, on the other hand, severely injured with Sigotoka disease (*Mycosphaerella musicola*), and the yields are greatly reduced.

In addition to the field spray, the harvested fruit are dipped into the 500 ppm suspension of active ingredients prior to storage and shipment. When the fruit reach the market the treated fruit are healthy and free of decay. The bananas which are not dip-treated prior to shipment, on the other hand, are badly rotted and supporting various molds including *Gloeosporium musarum*, *Botryodiplodia theobromae* and *Ceratocystis paradoxa*.

A similar post-harvest fruit dip may be used on citrus for the control of molds incited by *Penicillium digitatum*, *Penicillium italicum* and *Diplodia natalensis*.

I claim:

1. A fungicidal composition comprising a fungicidally effective amount of the mixture of methyl 2-benzimidazolecarbamate with the manganous or zinc salts of ethylenebisdithiocarbamic acid, the ratio of methyl 2-benzimidazolecarbamate to said manganous or zinc salts of ethylenebisdithiocarbamic acid being from 1:1 to 1:20.

2. The composition of claim 1 wherein the ratio of methyl 2-benzimidazolecarbamate to said managnous or zinc salts of ethylenebisdithiocarbamic acid being from 1:1 to 1:10.

3. A fungicidal composition of claim 1 comprising a fungicidally effective amount of the mixture of methyl 2-benzimidazolecarbamate with manganous ethylenebisdithiocarbamate, the ratio of methyl 2-benzimidazolecarbamate to said manganous ethylenebisdithiocarbamate being from 1:2 to 1:6.

4. A fungicidal composition of claim 1 wherein substantially all of the methyl 2-benzimidazolecarbamate and salt of ethylenebisdithiocarbamic acid has a particle size of less than five microns in diameter.

5. The method of preventing injury to plants due to fungi comprising applying to living plants a fungicidally effective amount of the mixture of claim 1.

6. The method of preventing injury to plants due to fungi comprising applying to living plants a fungicidally effective amount of the mixture of claim 3.

* * * * *